(12) United States Patent
Tsujita et al.

(10) Patent No.: US 6,800,057 B2
(45) Date of Patent: Oct. 5, 2004

(54) IMAGE OBTAINING APPARATUS

(75) Inventors: Kazuhiro Tsujita, Kaisei-machi (JP); Yukihiko Nakajima, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 0 days.

(21) Appl. No.: 10/156,693

(22) Filed: May 29, 2002

(65) Prior Publication Data
US 2003/0013937 A1 Jan. 16, 2003

(30) Foreign Application Priority Data
May 29, 2001 (JP) .......................................... 2001/160013

(51) Int. Cl.⁷ ............................ A61B 1/045; A61B 1/06
(52) U.S. Cl. ...................... 600/160; 600/109; 600/178; 600/181; 600/476
(58) Field of Search ................................ 600/160, 178, 600/109, 181, 476, 478; 250/458.1, 461.2; 348/65, 74, 76

(56) References Cited

U.S. PATENT DOCUMENTS

| | | | | |
|---|---|---|---|---|
| 5,335,075 A | * | 8/1994 | Komiya et al. | 348/298 |
| 5,337,340 A | * | 8/1994 | Hynecek | 377/60 |
| 5,729,288 A | * | 3/1998 | Saito | 348/243 |
| 5,749,830 A | * | 5/1998 | Kaneko et al. | 600/160 |
| 5,827,190 A | * | 10/1998 | Palcic et al. | 600/476 |
| 5,833,617 A | | 11/1998 | Hayashi | |
| 6,070,096 A | | 5/2000 | Hayashi | |
| 6,084,634 A | * | 7/2000 | Inagaki et al. | 348/294 |
| 6,217,510 B1 | * | 4/2001 | Ozawa et al. | 600/129 |
| 6,462,770 B1 | * | 10/2002 | Cline et al. | 348/65 |
| 6,516,217 B1 | * | 2/2003 | Tsujita | 600/477 |
| 6,529,768 B1 | * | 3/2003 | Hakamata | 600/476 |
| 2002/0013512 A1 | * | 1/2002 | Sendai et al. | 600/160 |
| 2002/0035330 A1 | * | 3/2002 | Cline et al. | 600/476 |

FOREIGN PATENT DOCUMENTS

| | | |
|---|---|---|
| EP | 1 099 405 A1 | 5/2001 |
| JP | 7-176721 | 7/1995 |
| JP | 9-308604 | 12/1997 |

* cited by examiner

*Primary Examiner*—John P. Leubecker
(74) *Attorney, Agent, or Firm*—Sughrue Mion, PLLC

(57) ABSTRACT

An accurate determination of the tissue state of a diseased portion is performed by use of an image obtaining apparatus employing a charge multiplying type solid state image obtaining element. A target subject is irradiated with an illuminating light that contains an excitation light, and the reflected light, which includes a fluorescence image, reflected from the target subject thereupon is detected by a charge multiplying type CCD. At this time, the fluorescent light image is passed through a rotating filter, and is detected as a wide band fluorescent light image and a narrow band fluorescent light image by the charge multiplying type CCD, and obtained as a wide band fluorescence image data and a narrow band fluorescence image data by an image processing unit. A fluorescence diagnostic image is obtained of the wide band fluorescence image data and the narrow band fluorescence image data, and displayed on a monitor.

15 Claims, 8 Drawing Sheets

IMAGE OBTAINING APPARATUS

BACKGROUND OF THE INVENTION

1. Field of the Invention

The present invention relates in general to an image obtaining apparatus for irradiating a target subject with an illuminating light and obtaining an optical image based on the re-radiated light re-radiated from said target subject upon the irradiation thereof by said illuminating light, and in particular to an image obtaining apparatus employing a charge multiplying type solid state image obtaining element to obtain images.

2. Description of the Related Art

There are known image obtaining apparatuses, which utilize a solid state image obtaining element such as a CCD or the like for converting an optical image to an electric signal, for obtaining an optical image of a target subject. In recent years, as described, for example, in Japanese Unexamined Patent Publication No. 7(1996)-176721, charge multiplying type solid state image obtaining elements for multiplying an obtained signal charge by a multiplication rate based on a multiplication rate control signal have been developed; wherein, by providing this charge multiplying type solid state image obtaining element, the image obtaining sensitivity of the image obtaining apparatus can be improved and controlled. That is to say, even if the light quantity of an optical image is insufficient to be obtained as an image utilizing a conventional image obtaining apparatus, if said optical image is obtained by use of this charge multiplying type solid state image obtaining element, said optical image can be displayed as a visible image; moreover, the image obtaining sensitivity can be controlled so as to match the image obtaining conditions. A charge multiplying type solid state image obtaining element provided with a charge multiplying means such as that described above is called a CMD (Charge Multiplying Detector) –CCD; wherein, conduction electrons and atoms are made to collide within a high-intensity electric field region, and the charge multiplication effect produced by this ionization serves to multiply the signal charge, whereby the image obtaining sensitivity can be improved.

According to a charge multiplying type solid state image obtaining element, because the charge multiplying means is a means for multiplying the signal charges which is situated in a series of signal processing means in the signal processing sequence as the means before a charge detecting circuit for converting the signal charges into sequential signal voltages and obtaining said voltages as an output signal, the charge multiplying means does not multiply the readout noise produced by the charge detecting circuit, the S/N ratio can be improved thereby. Accordingly, by using a charge multiplying type solid state image obtaining element, it becomes possible to improve the S/N ratio of the output signals of an imaging device that performs image obtainment under conditions in which there is insufficient light for an optical image. Further, because the signal charge multiplication rate can be changed by the multiplication rate control signal, it becomes possible to control the image obtaining sensitivity of an image obtaining apparatus provided with a charge multiplying type solid state image obtaining element.

Further, endoscope apparatuses employing a solid state image obtaining element are in wide use. By displaying the images obtained by a CCD on a monitor or the like, these endoscope apparatuses feature the advantage of being able to allow observation of the image by a plurality of people simultaneously. In addition, by subjecting an obtained image to various image processes before displaying said image, characteristics of the image can be enhanced and the image displayed on a monitor, making a great contribution to the advancement of medicine.

According to these endoscope apparatuses, making use of the fact that the intensity of the fluorescent light emitted from a normal tissue differs from the intensity of the fluorescent light emitted from a diseased tissue when a target subject (i.e., a living tissue) is irradiated by an excitation light having a predetermined wavelength, by detecting the fluorescent light emitted from a target subject upon irradiation thereof by an excitation light having a predetermined wavelength, the location and range of penetration of a diseased tissue is displayed as a fluorescence image, and the tissue state of a diseased portion is determined. However, because there is unevenness on the surface of a target subject, the distance between the light emitting system for emitting the excitation light and the target subject is not uniform; therefore, the intensity of the excitation light irradiating the target subject is generally not of a uniform intensity. Further, although the intensity of the fluorescent light emitted from the target subject is substantially proportional to the intensity of the excitation light, the intensity of the aforementioned excitation light becomes weaker in inverse proportion to the square of the distance between the excitation light and the target subject. Therefore, there are cases in which the fluorescent light emitted from a diseased tissue located at a position closer to the excitation light source than a normal tissue is of a higher intensity than the fluorescent light emitted from aforementioned normal tissue. Under such conditions, if an observer of an image obtained by the use of the above-described apparatus makes a determination as to the tissue state of the target subject based solely on the data relating to the intensity of the fluorescent light received from the target subject upon the irradiation thereof with an excitation light, there will be cases in which a false determination of the tissue state of the target subject will be made.

In order to mitigate the negative effects of the problems described above, there has been described an image display apparatus in Japanese Unexamined Patent Publication No. 9(1997)-308604, wherein: two types of fluorescence images, e.g., a narrow band fluorescence image having a wavelength near 480 nm, in which the difference in the intensity of the fluorescent light emitted from a normal tissue and the intensity of the fluorescent light emitted from a diseased tissue is large, and a wide band fluorescence image formed of light having wavelengths within the visible spectra of 430–730 nm, for example, are obtained; the ratio of the intensity of the narrow band fluorescence image and the wide band fluorescence image is obtained; and a pseudo color image is displayed based on this ratio. By obtaining the ratio described above, because the factor of the dependency of the intensity of the fluorescent light on the distance between the excitation light source and the fluorescent light receiving portion, and the target subject is cancelled, it is possible to form an image in which only the difference in the spectral form of the fluorescent light is reflected.

On the other hand, the miniaturization of the diameter of the endoscope has seen progress in recent years, and whereas in the past endoscopes were limited to being employed to examine the intestinal tract, currently, endoscopes are employed to examine the respiratory tract, the otorhinolaryngological cavity and passages, and the joints. However, because the number of light guiding fibers for transmitting the illuminating light becomes limited in accordance with the miniaturization of the endoscope, there are cases for which it is not possible to emit sufficient illuminating light; therefore, there is a demand for the development of an image obtaining apparatus capable of obtaining images at a desired image obtaining sensitivity. Further, fluorescence image observation of the fluorescence image obtained of the fluorescent light emitted from a target subject upon the irradiation thereof by an excitation light is also performed. Because the fluorescent light emitted from a target subject upon the irradiation thereof by an excitation light is extremely faint, there are cases in which the obtainment thereof as an image is impossible with current apparatuses; therefore, there is a demand for the development of an image obtaining apparatus capable of obtaining images at a desired image obtaining sensitivity. In order to solve these problems, the structure of and the method of controlling the image obtaining sensitivity for an apparatus wherein the charge multiplying type solid state image obtaining element is installed in an endoscope apparatus have been described in Japanese Unexamined Patent Publication No. 2001-29313

However, the even in an endoscope apparatus employing a charge multiplying type solid state image obtaining element, there are cases in which the fluorescent light emitted from a diseased tissue located at a position closer to the excitation light source than a normal tissue is of a higher intensity than the fluorescent light emitted from aforementioned normal tissue. Therefore, if an observer of an image obtained by the use of the above-described apparatus makes a determination as to the tissue state of the target subject based solely on the intensity of the fluorescent light received from the target subject upon the irradiation thereof with an excitation light, there will be cases in which a false determination of the tissue state of the target subject will be made.

SUMMARY OF THE INVENTION

The present invention has been developed in consideration of the circumstances described above, and it is an object of the present invention to provide an image obtaining apparatus such as an endoscope apparatus or the like employing a charge multiplying type solid state image obtaining element that is capable of obtaining images in which the tissue state of a target subject can be accurately discerned.

The image obtaining apparatus according to the present invention comprises: a light emitting means for projecting an illuminating light that includes an excitation light onto a target subject; and a charge multiplying type solid state image obtaining element for obtaining an optical image based on the re-radiated light, which contains fluorescent light, re-radiated from the target subject upon the irradiation thereof by the illuminating light, and obtaining an output data representing the obtained optical image; wherein the solid state image obtaining element is an element for obtaining fluorescence images based on fluorescent light of mutually different wavelength ranges.

The referent of "excitation light" includes light having a wavelength in the 400–420 nm wavelength range.

The referents of "illuminating light" include, for example, aside from the excitation light, white light, light in the three primary color wavelength ranges, which are sequentially emitted, and near-infrared light, which is not readily absorbed by the target subject.

Note that the light emitting means can be a means of a configuration employing a simple white light source, wherein a filter that transmits the light in the excitation light wavelength range and other wavelength ranges is used to change the wavelength of the illuminating light projected onto the target subject. Further, the light emitting means can be a means of a configuration employing a light source that emits excitation light, and a light source that emits light in the other wavelength ranges; wherein the wavelength range of the illuminating light projected onto the target subject is sequentially changed by switching between a mode in which the excitation light source is driven and a mode in which the other light source is driven.

The "re-radiated light" refers to the light generated by the target subject upon the irradiation thereof by the illuminating light; more specifically, the "re-radiated light" includes the fluorescent light emitted from a target subject upon the irradiation thereof by the excitation light, the reflected light reflected from the target subject upon the irradiation thereof by the white light, the light in the three primary color wavelength ranges or the near-infrared light, or the scattered light scattered at and emitted from the vicinity of the surface of the target subject.

Therefore, the image obtaining apparatus according to the present invention can obtain a diagnostic fluorescence image based on the fluorescent light emitted from a target subject upon the irradiation thereof by the excitation light, and a reflectance image based on the reflected light reflected from the target subject upon the irradiation thereof by a white light or the like.

The expression "obtaining fluorescence images based on fluorescent light of mutually different wavelength ranges" refers to the utilization of an optical means such as a filter or a prism to extract fluorescent light having mutually different wavelength ranges from the fluorescent light emitted from the target subject upon the irradiation thereof by the excitation light, and forming a respective fluorescence image from each of said fluorescent light of mutually different wavelength ranges. For example, a narrow band fluorescence image formed based on the fluorescent light that has passed through a narrow band filter that transmits light having a wavelength near 480 nm, and a wide band fluorescence image formed based on the fluorescent light that has passed through a wide band filter that transmits light having wavelengths in the 400–750 nm wavelength range may be obtained.

Note that according to the image obtaining apparatus of the present invention, it is preferable that a correcting means for detecting the dark noise generated by the solid state image obtaining means, and correcting the output data, based on the detected dark noise, to obtain a corrected output data is provided.

The referent of "dark noise" includes not only the dark noise obtained of the solid state image obtaining means, but also, for the case in which the image obtaining apparatus of the present invention is employed in an endoscope apparatus, for example, the noise generated due to the external light transmitted through living tissue.

In this case, the correcting means can be a means for: causing the emission of the illuminating light from the light emitting means on to the target subject to be paused periodically at regular intervals; detecting the dark noise based on the output signal obtained by the solid state image obtaining means during the interval in which the emission of said illuminating light has been paused; and correcting, based on the dark noise, the output data obtained by the solid state image obtaining means during the interval in which the illuminating light has been projected onto the target subject to obtain a corrected output data.

Further, the correcting means can be a means for correcting the output data representing the fluorescence image.

Still further, the image obtaining apparatus according to the present invention may further comprise a rotating filter means having at least two filter elements, each of which transmits a different wavelength range of light; wherein, by the rotation of the different filter elements, each of said filter elements can be made to positionally correspond with the light receiving surface of the solid state image obtaining means.

In addition, according to the image obtaining apparatus of the present invention, the solid state image obtaining means can be provided on the light receiving surface thereof with a filtering means formed of a combination of a plurality of two types of filter elements, each of which transmits a different wavelength range of light, disposed alternately on a two-dimensional flat surface.

Further, according to the image obtaining apparatus of the present invention, a portion or the entirety of the light emitting means and the solid state image obtaining means can be provided in the form of an endoscope for insertion into a body cavity of a patient.

According to the present invention, an image obtaining apparatus comprising a solid state image obtaining element provided with a charge multiplying means obtains fluorescence images based on fluorescent light having mutually different wavelength ranges. In this manner, by obtaining the ratio of the output data representing these fluorescence images, the factor of the distance between the target subject and the re-radiated light can be cancelled, and an image reflecting only the difference between the intensities of the spectra of the fluorescent light can be obtained. Accordingly, the tissue state of the target subject can be accurately discerned.

Here, when the ratio of the output data is to be obtained, particularly if the S/N ratio of the output data, which is the denominator is poor, the ratio is changed by a large amount, and the accuracy of the distinguishability of the tissue state of the target subject is reduced. On the other hand, the noise of the output data obtained by a solid state image obtaining element provided with a charge multiplying means is controlled. Therefore, by detecting the dark noise generated by the solid state image obtaining means, and correcting the output data based on the dark noise, the noise component of the output data can be reduced and the S/N ratio improved thereby. Accordingly, the ratio between the output data representing the fluorescence images can be obtained more accurately; as a result, the distinguishability of the tissue state of the target subject can be improved.

Here, while the emission of the illuminating light from the light emitting means onto the target subject is paused, the output signal obtained by the solid state image obtaining means represents the dark noise of the solid state image obtaining means. Accordingly, by pausing the emission of the illuminating light from the light emitting means onto the target subject and obtaining the output signal of the solid state image obtaining means during the interval in which the emission of the illuminating light is paused, the dark noise of the solid state image obtaining means can be easily detected. Further, by periodically detecting the dark noise of the solid state image obtaining means at regular intervals and correcting the output data obtained by the solid state image obtaining means during the interval in which the illuminating light is being projected onto the target subject, even if the dark noise changes, because correction data reflecting the change in the dark noise can be obtained, the ratio between the output data can be obtained accurately, and the tissue state of the target subject can be discerned more accurately.

In particular, because the intensity of the fluorescent light is extremely weak, if the output data representing the fluorescence images is corrected, fluorescence images having a further improved S/N ratio can be obtained, and as a result, the tissue state of the target subject can be discerned more accurately.

Further, by providing the rotating filter means, because different wavelength ranges of transmitted fluorescent light can be easily projected onto the solid state image obtaining means, the fluorescence images can be easily obtained. Further, because it is easy to provide the rotating filter means with a filter element that transmits wavelengths of light other than that of the excitation light (e.g., light in the three primary color wavelength ranges, near-infrared wavelengths, etc.), fluorescence image based on various wavelength ranges of light can be easily obtained. In this case, because it becomes unnecessary to provide solid state image obtaining means corresponding to various wavelength ranges of light, the configuration of the apparatus can be simplified.

Still further, by providing on the light receiving surface the of the solid state image obtaining means a filtering means formed of a combination of a plurality of two types of filter elements, each of which transmits a different wavelength range of light, disposed alternately on a two-dimensional flat surface, fluorescence images based on a different wavelength ranges of light can be obtained by a use of a simplified configuration; whereby the configuration of the image obtaining apparatus can be simplified. In particular, if the obtainment of fluorescence images formed of light of a plurality of mutually different wavelength ranges is performed based on light that has been transmitted by the wide band filter element, because it becomes unnecessary to provide solid state image obtaining means corresponding to various wavelength ranges of light, the configuration of the apparatus can be further simplified.

DESCRIPTION OF THE PREFERRED EMBODIMENTS

Figure 1:
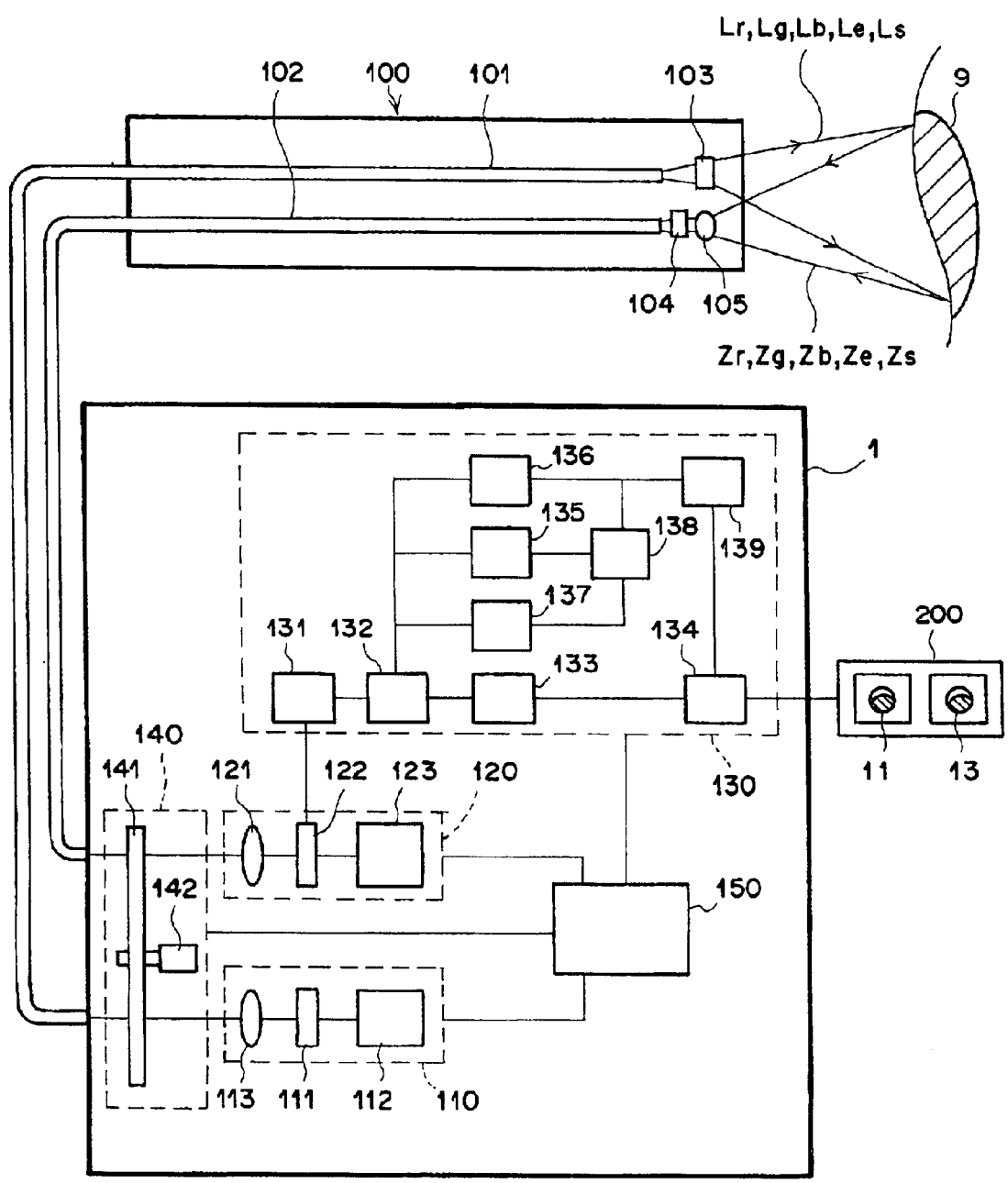
FIG. 1 is a schematic drawing of an endoscope apparatus implementing the image obtaining apparatus according to the first embodiment of the present invention.

Hereinafter the preferred embodiments of the present invention will be explained with reference to the attached drawings. FIG. 1 is a schematic drawing of a fluorescent endoscope apparatus implementing the fluorescence image display apparatus according to first embodiment of present invention. As shown in FIG. 1, the fluorescent endoscope according to the first embodiment is a planar sequence type endoscope apparatus, wherein: illuminating light consisting of R light (red light) Lr, G light (green light) Lg, B light (blue light) Lb, reference light (near-infrared light) Ls, and excitation light Le, is sequentially projected onto a target subject 9; a fluorescence image formed of the fluorescent light emitted from the target subject 9 upon the irradiation thereof by the excitation light, and reflectance images formed of the reflected light reflected from the target subject upon the irradiation thereof by the light other than the excitation light are obtained by a charge multiplying type CCD image obtaining element; and a color image of the target subject is displayed on a monitor. The fluorescent endoscope according to the current embodiment comprises: an endoscope insertion portion 100 to be inserted into the primary nidus and areas of suspected secondary infection of a patient; an image data processing portion 1 for processing the image data representing the data obtained of the target subject 9; and a monitor 200 for displaying the image data processed by the image data processing portion 1 as a visible image.

The image data processing portion 1 comprises: an illuminating unit 110 provided with a light source for emitting illuminating light; an image detecting unit 120 for obtaining reflectance images Zr, Zg, and Zb, which are formed of the reflected light reflected from the target subject 9 upon the irradiation thereof by the R light Lr, the G light Lg, and the B light Lb, respectively, a fluorescence image Ze, which is formed of the fluorescent light emitted from a target subject 9 upon the irradiation thereof by the excitation light Le, and a reflectance image Zs (hereinafter referred to as an optical image), which is formed of the reflected light reflected from the target subject 9 upon the irradiation thereof by the reference light Ls, converting each of said obtained images to digital values to obtain image data thereof, and outputting said image data; an image processing unit 130 for subjecting the image data to the images processes required to display said image data as visible images; a filtering unit 140 for controlling the wavelength range of the illuminating light emitted from the light emitting means 110 and the wavelength range of the optical image inputted to the image processing portion 120; and a controller 150 for controlling the operation of each unit.

The endoscope insertion portion 100 is provided with a light guide 101 extending internally to the distal end thereof, and an image fiber 102. An illuminating lens 103 is provided at the distal end portion of the light guide 101, that is, at the distal end of the endoscope insertion portion 100. Further, the image fiber 103 is formed of a composite glass fiber, and an excitation light cutoff filter 104 for cutting off the excitation light and a focusing lens 105 are provided at the distal end portion thereof. The excitation light cutoff filter 104 is a long pass filter that transmits all light having a wavelength greater than or equal to 420 nm. The distal end portion and the opposite end portion of light guide 101 are connected to the illuminating unit 110 via the filtering unit 140. The distal end of the image fiber 102 is connected to the image detecting unit 120 via the filtering unit 140.

The illuminating unit 110 comprises: a white light source 111, which is a xenon lamp that emits white light; a white light source power source 112 electrically connected to the white light source 111; and a white light focusing lens 113 for focusing the white light emitted from the white light source 111.

The image detecting unit 120 comprises: a focusing lens 121 that is connected to the image fiber 102 and which focuses an optical image conveyed thereto via the image fiber 102; a charge multiplying type CCD image obtaining element 122 for obtaining the focused image; and a CCD controller 123 for controlling the operation of the CCD image obtaining element 122.

Figure 2:
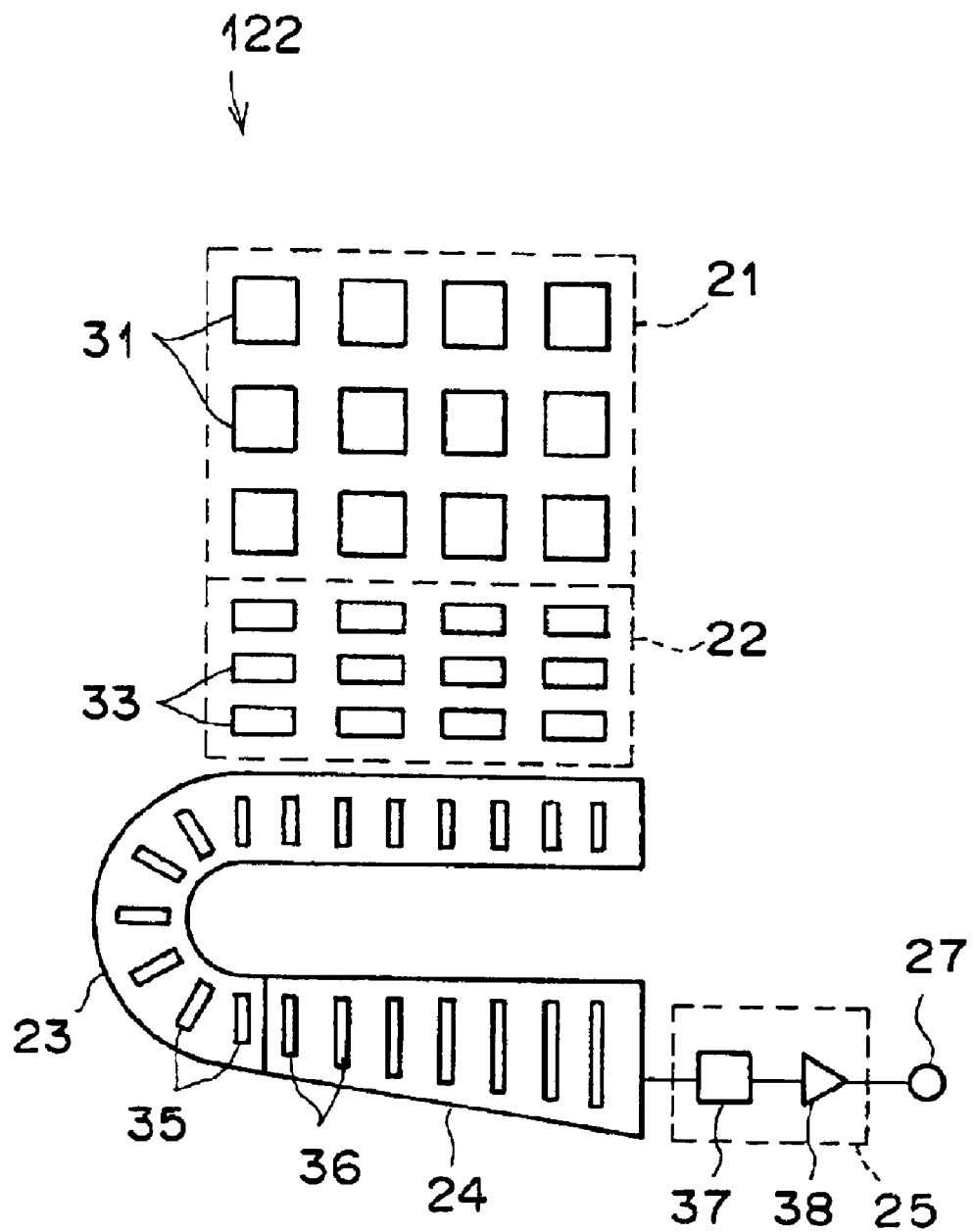
FIG. 2 is schematic drawing of the configuration of a CCD image obtaining element.

FIG. 2 shows the configuration of the CCD image obtaining element 122. As shown in FIG. 2, the CCD image obtaining element 122 is a frame transfer type CMD-CCD, comprising: a light receiving portion 21 for converting an obtained optical image to signal charges; a horizontal transfer portion 23 for horizontally transmitting the signal charges; a charge multiplying portion 24 for multiplying the signal charges, based on the inputted multiplication rate control signal; and an outputting portion 25 for converting the signal charges from the charge multiplying portion 24 to signal voltages, amplifying said voltages and outputting the amplified signal voltages to the image processing unit 130 via the output terminal 27.

The light receiving portion 21 is formed of a number n vertical and a number n' horizontal of vertically transmitting CCD elements 31 for performing photoelectric conversion and transmitting signal charges vertically. For the sake of simplicity in explanation the light receiving portion 21 shown in FIG. 2 comprises 3 vertical and 4 horizontal vertically transmitting CCD elements 31; however, an actual CCD image obtaining element 122 is provided with several hundred vertically transmitting CCD elements 31 in both the vertical and horizontal positions.

The accumulating portion 22 is shielded from light by use of a thin metallic film or the like, and comprises a vertically transmitting CCD 33 for temporarily accumulating signal charges and performing vertical transmission thereof. The horizontal transmitting portion 23 is formed of a horizontally transmitting CCD 35.

The charge multiplying portion 24 is formed of an m number of charge multiplying cells 36. The signal charges inputted to the charge multiplying portion 24 are multiplied and sequentially transmitted, based on a multiplication rate control signal which is a continuous pulse type signal. The charge multiplication cells 36 cause conduction electrons and atoms to collide within a high-intensity charge region, wherein the inputted signal charges are multiplied by use of the charge multiplication effect produced by the resulting ionization, and then outputted; the multiplication rate thereof is changed based on the signal characteristics of the aforementioned multiplication rate control signal. Note that the accumulating portion 22, the horizontal transmitting portion 23, and the charge multiplying portion 24 shown in FIG. 2 are also of a simplified configuration in the same manner as the light receiving portion 21.

The outputting portion 25 comprises a charge detecting portion 37 for converting signal charges to signal voltages (output signals), and an output amplifier 38 for amplifying the output signals.

The CCD controller 123 is a means for outputting an operation control signal for controlling the operational timing of the CCD image obtaining element 122, and a multiplication rate control signal for controlling the multiplication rate of the charge multiplying means 24. By outputting a multiplication rate control signal based on a desired peak value set by an operator, the multiplication rate of the charge multiplying means 24 can be controlled.

The image processing unit 130 comprises: a signal processing circuit 131 for processing the image signals obtained by the CCD image obtaining element 122; an A/D converting circuit 132 for digitizing the image data obtained by the signal processing circuit 131; an image memory 133 for storing the image data obtained of each color reflectance image, Zr, Zg, and Zb; a fluorescence image memory 135 for storing a wide band fluorescence image represented by a wide band fluorescence image data and a narrow band fluorescence image represented by a narrow band fluorescence image data, which are obtained from the fluorescence image Ze as described below; an image memory 136 for storing a reference image data obtained from the reflectance image Zs; a dark noise memory 137 for recording the dark noise data obtained by the A/D conversion of the signal obtained at the CCD image obtaining element 122 while said CCD image obtaining element 122 is in the state of not being irradiated by the illuminating light; a correcting circuit 138 for subtracting the dark noise from data from the wide band fluorescence image data and the narrow band fluorescence image data stored in the image memory 135 to correct said wide band fluorescence image data and narrow band fluorescence image data; an image forming circuit 139 for correlating each pixel of the wide band fluorescence image represented by the wide band fluorescence image data to each corresponding pixel of the narrow band fluorescence image represented by the narrow band fluorescence image data, which have been correcting by the correcting circuit 139, and computing the ratio therebetween to obtain a computed value for each pixel, assigning color data to each of said pixels corresponding to the size of the computed value thereof to form a color image data representing a color image, assigning brightness data to each of the pixels of the reference image represented by the reference image data to form a brightness image data representing a brightness image, and combing the color image data and the brightness image data to form a composite image data representing a diagnostic fluorescence image; and a video signal processing circuit 134 for converting and outputting as video signals the three color image data stored in the image memory 133, which are synchronized and outputted therefrom simultaneously, and the composite image data formed by the image forming circuit 139.

Note that the image forming circuit 139 can be a means for correlating each of the respective pixels of the wide band fluorescence image represented by a wide band fluorescence image data and a narrow band fluorescence image represented by a narrow band fluorescence image data stored in the image memory 135 and the reference image represented by the reference image data stored in the image memory 136 and computing the ratio therebetween to obtain a computed value for each pixel, and assigning a color data to each pixel based on the size of the computed value thereof to form a color image data.

The filter unit 140 comprises a rotating filter 141 for sequentially changing the wavelength range of the white light emitted from the illuminating unit 110, and a motor 142 for rotating the rotating filter 141.

Figure 3:
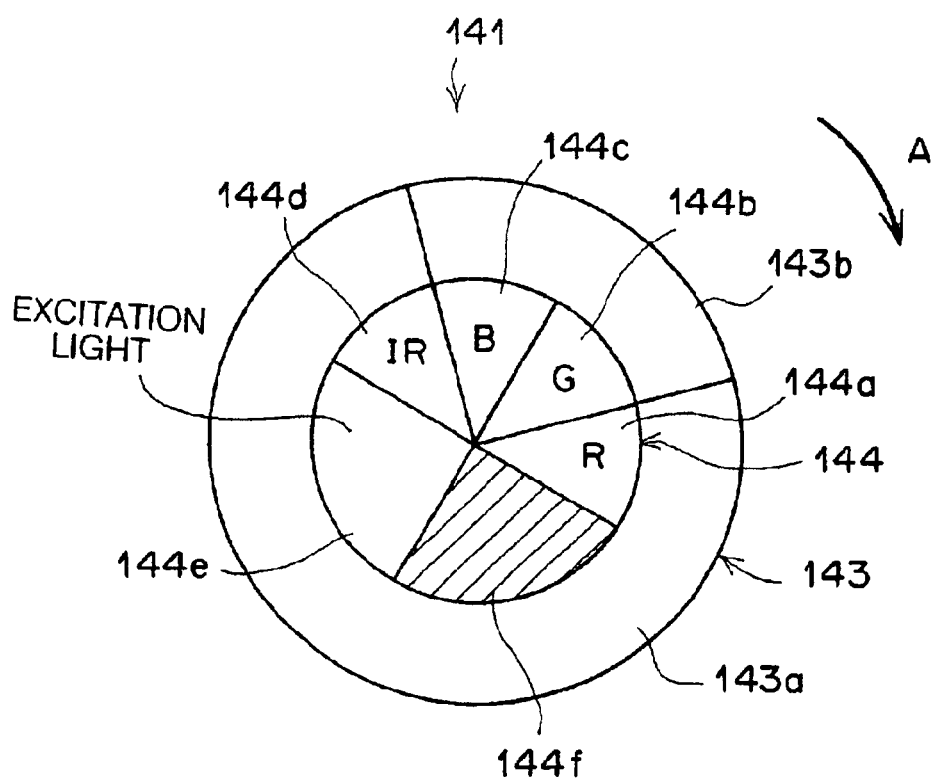
FIG. 3 is a schematic drawing of the rotating filter of the first embodiment of the present invention.

The configuration of the rotating filter 141 is shown in FIG. 3. As shown in FIG. 3, the rotating filter 141 is divided into an inner circumference region 14 and an outer circumference region 143; further, the outer circumference portion 143 is formed of a wide band filter element 143a that passes all wavelengths of light in the 400–900 nm wavelength range, and a narrow band filter element 143b that transmits light having wavelengths in the 430–530 nm wavelength range. On the other hand, the inner circumference portion 144 of filter elements 144a–144e for transmitting light having a wavelength in the R, G, B wavelength ranges, and the 750–900 nm infrared wavelength range, and a filter element 144f for shielding the excitation light, which has a wavelength of 410 nm. Further, the optical image guided by the image fiber 102 is projected onto the outer circumference portion 143 of the rotating filter 141, and when the rotating filter 141 is rotated in the direction indicated by the arrow A, the optical image is passed through the wide band filter element 143a and the narrow band filter element 143b and detected by the CCD image obtaining element 122. Further, the white light emitted from the illuminating unit 110 is projected onto the inner circumference portion 144, and the R light Lr, G light Lg, B light Lb, the near-infrared light, and the excitation light are projected onto the target subject 9 via the light guide 101 by the rotation of the rotating filter 141.

Note that the cycle of the emission of the R light, G light, B light near-infrared light, and the excitation light onto the target subject 9, and the shielding of the illuminating light is repeated by the rotation of the rotating filter 141. Here, during the interval in which the R light Lr, G light Lg, B light Lb, and the near-infrared light are emitted, the optical image guided by the image fiber 102 is passed through the wide band filter element 143a. During the interval in which the excitation light Le is emitted, the optical image guided by the image fiber 102 is passed through each of the wide band filter element 143a and the narrow band filter element 143b. Further, during the interval in which the illuminating light is shielded, although external light transmitted through the target subject 9 enters the image fiber 102, the external light is passed through the each of the wide band filter element 143a and the narrow band filter element 143b, in the same manner as the excitation light Le.

Hereinafter the operation of the endoscope apparatus according to the first embodiment will be explained. The endoscope apparatus according to the first embodiment performs the obtainment of the reflectance images Zr, Zg and Zb, the reflectance image Zs, the fluorescence image Ze, and the detection of the dark matter in a time division manner; wherein a standard image 11 base on the reflectance images Zr, Zg and Zb, and a fluorescence diagnostic image based on the reflectance image Zs and the fluorescence image Ze are displayed on a monitor 200. Because each optical image is obtained in a time division manner, the rotating filter 141 of the filtering unit 141 is rotated, and by passing the white light emitted from the illuminating unit 110 through the inner circumference region of the rotating filter 141, the the R light Lr, G light Lg, B light Lb, the reference light Ls, and the excitation light Le and are sequentially projected onto the target subject 9.

First, the operation occurring when a standard image 11 is to be obtained will be explained. First, when the R light Lr is projected onto the target subject 9, a reflectance image Zr formed of the light reflected from the target subject 9 upon the irradiation thereof by the R light Lr is focused by the focusing lens 105, passed through the excitation light cutoff filter 104 and enters the distal end of the image fiber 102; then, said reflectance image Zr enters the outer circumference region 143 of the rotating filter 141 via the image fiber 102. Because the outer circumference region 143 of the rotating filter 141 is configured so as to pass the optical images reflected from the target subject 9, during the intervals in which the R light Lr, G light Lg, and B light Lb, respectively, are being projected onto said target subject 9, through the wide band filter element 143a, the reflectance image Zr is passed through the wide band filter element 143a and enters the image detecting unit 120. The reflectance image Zr that has entered the image detecting unit 120 is transmitted by the focusing lens 121 and focused onto the CCD image obtaining element 122.

The reflectance image Zr is received by the vertically transmitting CCD elements 31 of the light receiving portion 21 of the CCD image obtaining element 122, and is converted to electric signals corresponding to the intensity level of the photoelectrically converted light.

After the passing of a predetermined period of time, the rotating filter 141 is rotated, and the filter element disposed along the optical path of the white light emitted from the illuminating unit 110 is switched from the R light filtering element 144a to the G light filtering element 144b. At this time, the signal charges accumulated on the vertically transmitting CCD elements 31 are transmitted to the vertically transmitting CCD elements 33 of the accumulation portion 22.

The signal charges transmitted to the CCD elements 33 of the accumulation portion 22 are transmitted vertically in an array, and is received sequentially at the CCD elements 35 of the horizontally transmitting portion 23.

When the signal charges of a one horizontal line portion of pixels are inputted to the horizontal transmitting portion 23, said signal charges are transmitted in the horizontal direction to the charge multiplying cells 36 of the sequential charge multiplying portion 24. The charge multiplying cells 36 multiply and sequentially transmit, based on the multiplication rate control signal, said signal charges. The signal charge outputted from the last of the charge multiplying cells 36 to the outputting portion 25 located to the right of the charge multiplying portion 24 is converted to a signal voltage by the charge detecting portion 37, amplified by the output amplifier 38, and outputted from the outputting terminal 27 as an output signal.

Then, the next one horizontal line portion of signal charges is transmitted from the accumulating portion 22 to the horizontal transmitting portion 23. By the repetition of this type of operation, the signal charges of the pixels of the light receiving portion 21 are sequentially read out from the lower left side to the right side of the light receiving portion 21. When a one horizontal line portion of signal charges has been read out, the signal charges of the horizontal line above the line that has been read out is read out next; whereby the entire signal charge forming the R light reflectance image Zr is read out by sequentially moving to the next line up until the signal charges of all lines have been sequentially read out.

Note that while the readout of the charge signals accumulated on the charge accumulation portion are being read out, the G light Lg is projected onto the target subject 9, and the reflectance image Zg formed of the G light reflected from said target subject 9 is received at the CCD image obtaining element 122 via the image fiber 102 and the wide band filter element 143a of the rotating filter 141. Further, the image obtainment operation of the CCD image obtaining element 122 is performed based on operation control signals inputted thereto from the CCD controller 123.

The output data of the R light reflectance image Zr image is subjected to image processes by the signal processing circuit 131 of the image processing portion 130, digitized by the A/D converting circuit 132, and stored in the R light reflectance image Zr data region of the image memory 133.

Then, the G light reflectance image Zg image data and the B light reflectance image Zb image data are obtained by the same operation as that described above, and stored in the respective G light reflectance image Zg data region and B light reflectance image Zb data region of the image memory 133.

When the image data for the three colors have been stored in the image memory 133, said three images are synchronized and outputted simultaneously to the video signal processing circuit 134. The video signal processing circuit 134 converts said inputted signals to video signals and outputs said video signals to the monitor 200, and said video signals are displayed thereon as a standard image 11, which is a color image.

Next, the operation occurring when a fluorescence diagnostic image 13 is to be obtained will be explained. The rotating filter 141 is rotated, based on control signals from the controller 150, from the filter element 144c to the filter element 144d; wherein, the filter element 144d is positioned along the optical path of the white light emitted from the illuminating unit 110. In this manner, the reference light Ls, which is a near-infrared light, is projected onto the target subject 9.

The reflectance image Zs formed of the light reflected from the target subject 9 upon the irradiation thereof by the reference light Ls is focused by the focusing lens 105, passed through the excitation light cutoff filter 104, and enters the distal end of the image fiber 102; then, said reflectance image Zs enters the outer circumference region 143 of the rotating filter 141 via the image fiber 102. Because the outer circumference region 143 of the rotating filter 141 is configured so as to pass the optical image guided by the image fiber 102, during the interval in which the reference Ls is being projected onto said target subject 9, through the wide band filter element 143a, the reflectance image Zs passes through the wide band filter element 143a and enters the image detecting unit 120. The reflectance image Zs that has entered the image detecting unit 120 is transmitted by the focusing lens 121 and focused onto the CCD image obtaining element 122.

The reflectance image Zs is received by the CCD image obtaining element 122, converted to electric signals corresponding to the intensity level of the photoelectrically converted light, and outputted to the image signal processing portion 130 in the same manner as described above. The electric signals inputted to the image processing portion 130 are subjected to image processes by the signal processing circuit 131, digitized by the A/D converting circuit 132, and stored as reference image data in the image memory 136.

Next, the operation occurring when a fluorescence image Ze is to be obtained will be explained. The rotating filter 141 is rotated, based on control signals from the controller 150, from the filter element 144d to the filter element 144e; wherein, the filter element 144e is positioned along the optical path of the white light emitted from the illuminating unit 110. In this manner, the excitation light Le is projected onto the target subject 9.

The fluorescence image Ze formed of the light reflected from the target subject 9 upon the irradiation thereof by the excitation light Le is focused by the focusing lens 105, passed through the excitation light cutoff filter 104 and enters the distal end of the image fiber 102; then, said fluorescence image Ze enters the outer circumference region 143 of the rotating filter 141 via the image fiber 102. Because the outer circumference region 143 of the rotating filter 141 is configured so as to pass the optical image guided by the image fiber 102, during the interval in which the reference Ls is being projected onto said target subject 9, through the wide band filter element 143a and then the narrow band filter element 143b, the fluorescence image Ze is first passed through the wide band filter element 143a, and enters the image detecting unit 120 as a wide band fluorescence image. The wide band fluorescence image that has entered the image detecting unit 120 is transmitted by the focusing lens 121 and focused onto the CCD image obtaining element 122.

The wide band fluorescence image is received by the CCD image obtaining element 122, converted to electric signals corresponding to the intensity level of the photoelectrically converted light, and outputted to the image signal processing portion 130 in the same manner as described above. The electric signals inputted to the image processing portion 130 are subjected to image processes by the signal processing circuit 131, converted to digital signals by the A/D converting circuit 132, and stored in the wide band fluorescence image data region of the image memory 135.

Next, the fluorescence image Ze is passed through the narrow band filter element 143b and enters the image detecting unit 120 as a narrow band fluorescence image. A narrow band fluorescence image data is obtained thereof in the same manner as described above, and stored in the narrow band fluorescence image data region of the image memory 135.

Next, the operation occurring when the dark noise is to be obtained will be explained. The rotating filter 141 is rotated, based on control signals from the controller 150, from the filter element 144e to the filter element 144f; wherein, the filter element 144f is disposed along the optical path of the white light emitted from the illuminating unit 110. In this manner, light is not projected onto the target subject 9.

At this time, the external light transmitted through the target subject 9 is focused by the focusing lens 105, passed through the excitation light cutoff filter 104, and enters the distal end of the image fiber 102; then, said external light enters the outer circumference region 143 of the rotating filter 141 via the image fiber 102. Because the outer circumference region 143 of the rotating filter 141 is configured so as to pass the external light transmitted through the target subject 9, during the interval in which the dark noise is being detected, through the wide band filter element 143a, and then through the narrow band filter element 143b, the external light transmitted through the target subject 9 passes first through the wide band filter element 143a and then through the narrow band filter element 143b, and enters the image detecting unit 120. The external light that has entered the image detecting unit 120 is transmitted by the focusing lens 121 and focused onto the CCD image obtaining element 122.

The external light that has passed through the wide band filter element 143a and the narrow band filter element 143b is received by the CCD image obtaining element 122, converted to electric signals corresponding to the intensity level of the photoelectrically converted light, and outputted to the image signal processing portion 130 in the same manner as described above. The electric signals inputted to the image processing portion 130 are subjected to image processes by the signal processing circuit 131, digitized by the A/D converting circuit 132, and stored as a wide band dark level data and a narrow band dark level data in the dark noise memory 137. Note that these dark noise label data include the data not only of the external light transmitted by the target subject, but also of the dark noise of the CCD image obtaining element 122.

When the wide band dark level data and the narrow band dark level data are stored in the dark noise memory 137, the correcting circuit 138 subtracts the wide band dark level data and the narrow band dark level data from the wide band fluorescence image data and the narrow band fluorescence image data stored in the fluorescence image memory 135 to obtain a corrected wide band fluorescence image data and a corrected narrow band fluorescence image data.

When the corrected wide band fluorescence image data and the corrected narrow band fluorescence image data have been obtained, the image forming circuit 139 computes the ratio of the signal intensity between the corresponding pixels of the corrected wide band fluorescence image data and the corrected narrow band fluorescence image data, and applies a color data corresponding to said ratio to obtain a color image data. Further, the signal forming circuit 139 assigns a brightness data to the signal intensity of the reference image data to obtain a brightness image data, and then combines the color image data and the brightness image data to form a composite image data; the composite image data is outputted to the video signal processing circuit 134. The composite image data is converted to video signals by the video signal processing circuit 134 and outputted to the monitor 200. The video signals outputted to the monitor 200 are displayed thereon as a fluorescence diagnostic image 13, which is a pseudo color image.

Note that the fluorescent diagnostic image 13 is displayed as a pseudo color image; wherein, the display color thereof changes in accordance with the changes in the ratio of the relative intensities of the signal strength of the wide band fluorescence image data and the signal strength of the narrow band fluorescence image data, and the brightness thereof changes in accordance with the changes in the intensity of the reference image data. By setting the pseudo color image so that the difference between the display color of the fluorescent light emitted from the normal tissue and that emitted from the diseased tissue becomes clearer, the fluorescent light emitted from the normal tissue can be displayed as white, for example, and the fluorescent light emitted from the diseased tissue can be displayed as pink or another color. Therefore, the observer of the image can easily recognize a diseased tissue appearing therein. Further, because the brightness changes in accordance with the changes in the intensity of the intensity of the reference image data, a fluorescent diagnostic image wherein the unevenness of the surface of the target subject, the relative depth relation between tissues appearing in the image, and the like are discernable can be displayed.

In this manner, according to the endoscope apparatus of the current embodiment, which comprises a CCD image obtaining element 122 provided with a charge multiplying function, because a wide band fluorescence image and a narrow band fluorescence image can be obtained based on the fluorescent light of mutually different wavelength ranges, by obtaining the ratio between the signal values of the wide band fluorescence image and the narrow band fluorescence image, a fluorescence diagnostic image 13 representing the unevenness of the surface of the target subject, the relative depth relation between tissues appearing therein, and the like can be obtained. Accordingly, the tissue state of the target subject 9 can be accurately discerned.

Here, when the ratio of the wide band fluorescence image and the narrow band fluorescence image is to be obtained, particularly if the S/N ratio of the wide band fluorescence image, which is the denominator, is poor, the ratio changes by a large amount, and the accuracy with which the tissue state of the diseased portion can be discerned is reduced. On the other hand, the dark noise component of the noise of the wide band fluorescence image data and the narrow band fluorescence image data obtained by the charge multiplying type CCD image obtaining element 122 is controlled. Therefore, by detecting the dark noise generated by the CCD image obtaining element 122 and the dark level data formed from the external light transmitted by the target subject 9, and correcting the wide band fluorescence image data and the narrow band fluorescence image data based on the dark noise, the noise contained in the wide band fluorescence image data and the narrow band fluorescence image data can be reduced and the S/N ratio thereof improved thereby. Accordingly, the fluorescence diagnostic image 13 can be obtained more accurately; as a result, the accuracy with which the tissue state of the diseased portion can be discerned is improved.

Figure 4:
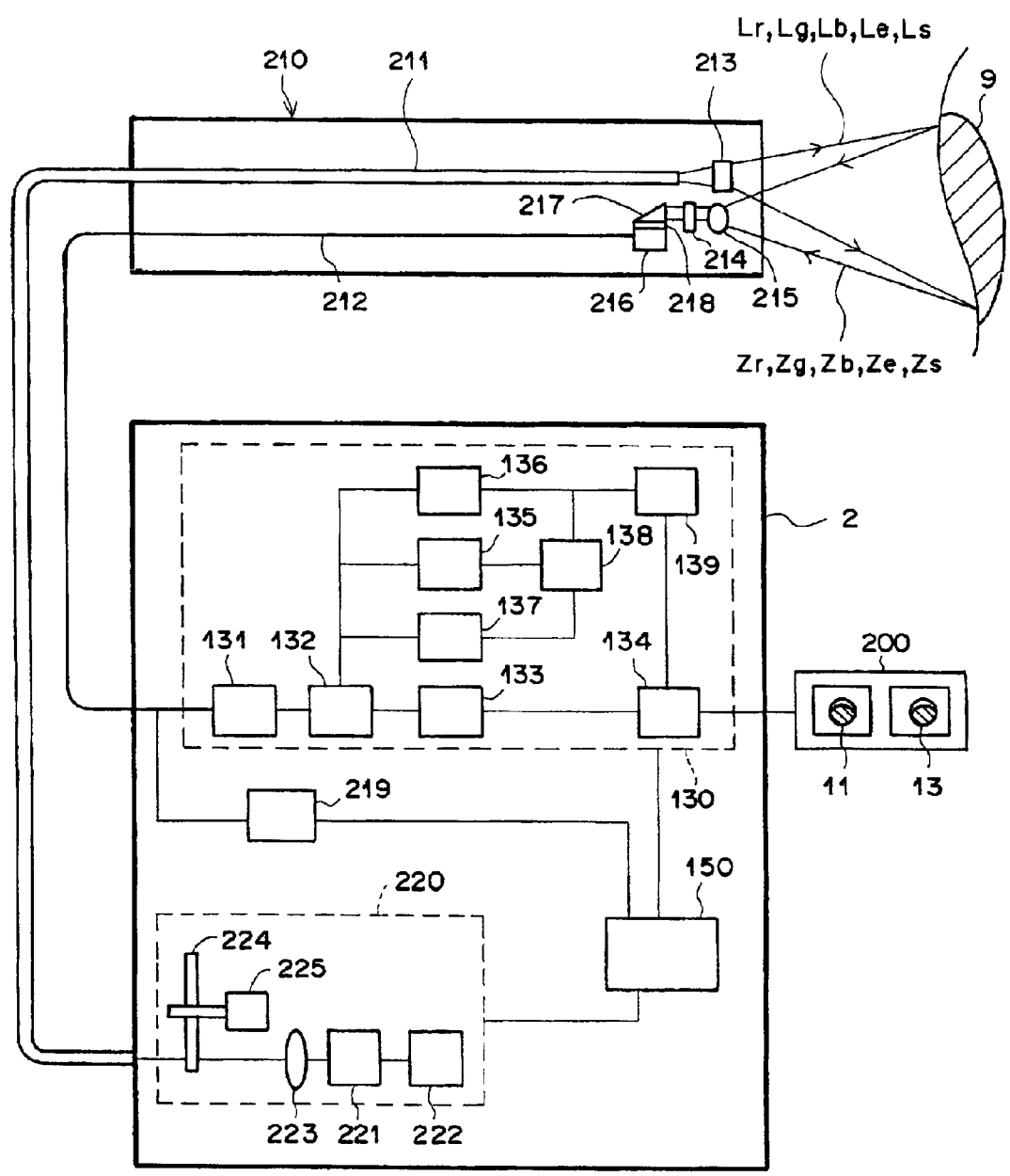
FIG. 4 is a schematic drawing of an endoscope apparatus implementing the image obtaining apparatus according to the second embodiment of the present invention.

Next, the second embodiment will be explained. FIG. 4 is a schematic drawing of a fluorescent endoscope apparatus implementing the fluorescence image display apparatus according to second embodiment. Note that elements of the fluorescent endoscope apparatus according to the second embodiment in common with those of the first embodiment are likewise labeled, and further explanation thereof has been omitted. The fluorescent endoscope apparatus according to the second embodiment sequentially projects R light Lr, G light Lg, B light Lb, reference light Ls, and excitation light Le, onto a target subject 9; wherein the reflected light reflected from the target subject 9 upon the irradiation thereof by each said light is obtained by a CCD image obtaining element 122 provided at the distal end of the endoscope.

Therefore, the fluorescent endoscope according to the second embodiment comprises: an endoscope insertion portion 210 to be inserted into the primary nidus and areas of suspected secondary infection of a patient; an image data processing portion 2 for processing the image data representing the data obtained of the target subject 9; and a monitor 200 for displaying the image data processed by the image data processing portion 2 as a visible image.

The endoscope insertion portion 210 is provided with a light guide 101 and a CCD cable 212 extending internally to the distal end thereof. An illuminating lens 213 an excitation light cutoff filter 214 and a focusing lens 215 are provided at the distal end portion of the light guide 211 and the CCD cable 212, that is, at the distal end of the endoscope insertion portion 210. A CCD image obtaining element 216, which is provided with an on-chip mosaic filter formed of a combination of micro wavelength range filter elements assembled in a mosaic pattern, is connected to the distal end of the CCD cable 212, and a prism 217 is attached to the CCD image obtaining element 216. Note that the CCD image obtaining element 216 is of the same configuration as the CCD image obtaining element 122 of the first embodiment.

Figure 5:
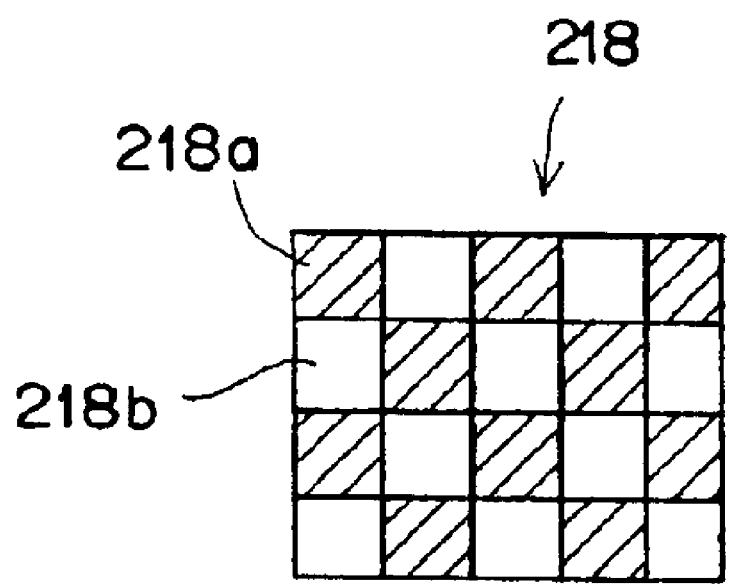
FIG. 5 is a schematic drawing of a mosaic filter.

FIG. 5 is a schematic drawing of the configuration of the mosaic filter 218. As shown in FIG. 5, the mosaic filter 218 is formed of a combination of wide band filter elements 218a that passes all wavelength of light in the 400–900 nm wavelength range, and narrow band filter elements 218b that transmit light having wavelengths in the 430–530 nm wavelength range, which are arranged alternately thereon; wherein each wavelength band filter element 218a, 218b is in a one-to-one correspondence with a pixel of the CCD image obtaining element 216.

The image processing portion 2 comprises: an illuminating unit 220 for emitting illuminating light; a CCD controller 219 for controlling the operations of the CCD image obtaining element 216; an image processing unit 130, which is the same as that of the first embodiment; and a controller 150, which is the same as that of the first embodiment, for controlling the operation of each unit and of the CCD controller 219.

The illuminating unit 220 comprises: a white light source 221, which is a xenon lamp that emits white light; a white light source power source 222 electrically connected to the white light source 221; a white light focusing lens 223 for focusing the white light emitted from the white light source 221; a rotating filter 224 for sequentially separating the white light into R light, G light, B light, reference light, and excitation light; and a motor 225 for rotating the rotating filter 224.

Figure 6:
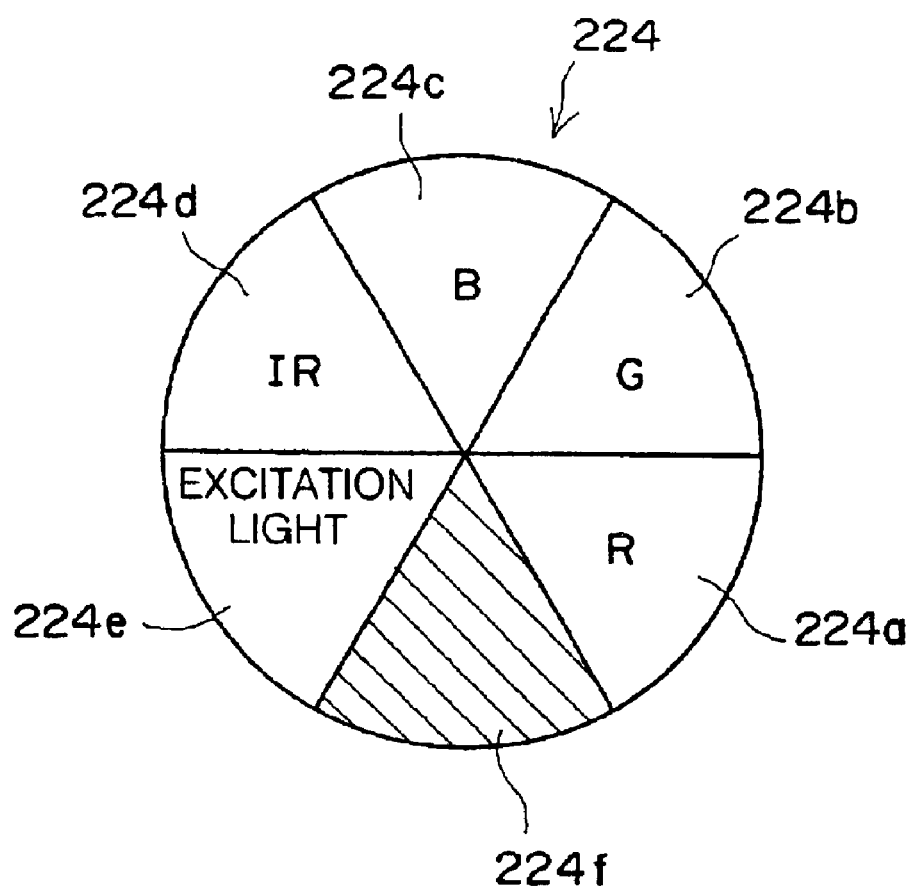
FIG. 6 is a schematic drawing of the rotating filter of the second embodiment of the present invention.

The configuration of the rotating filter 224 is shown in FIG. 6. As shown in FIG. 6, the rotating filter 224 is formed of filter elements 224a–224e for transmitting light having a wavelength in the R, G, B wavelength ranges, and the 750–900 nm infrared wavelength range (IR), and a filter element 224f for shielding the excitation light, which has a wavelength of 410 nm.

Note that the cycle of the emission of the R light, G light, B light near-infrared light onto the target subject 9, and the shielding of the excitation light is repeated by the rotation of the rotating filter 141. Here, during the interval in which the R light Lr, G light Lg, B light Lb near-infrared light are emitted, only the optical image passed through the wide band filter element 218a of the mosaic filter 218 is detected by the CCD image obtaining element 216. During the interval in which the excitation light Le is emitted, the fluorescence image passed through each of the wide band filter element 218a and the narrow band filter element 218b is detected by the CCD image obtaining element 216. Further, during the interval in which the excitation light is shielded, although the external light transmitted by the target subject 9 is detected, said external light passes through the each of the wide band filter element 218a and the narrow band filter element 218b, in the same manner as the excitation light Le.

Hereinafter the operation of the endoscope according to the second embodiment will be explained. The endoscope apparatus according to the second embodiment, in the same manner as the endoscope apparatus of the first embodiment, performs the obtainment of the reflectance images Zr, Zg and Zb, the reflectance image Zs, the fluorescence image Ze, and the detection of the dark matter in a time division manner; wherein a standard image 11 base on the reflectance images Zr, Zg and Zb, and a fluorescence diagnostic image based on the reflectance image Zs and the fluorescence image Ze are displayed on a monitor 200. Because each optical image is obtained in a time division manner, the rotating filter 224 of the illuminating unit 220 is rotated, and bypassing the white light emitted from the white light source 221 through the rotating filter 224, the the R light Lr, G light Lg, B light Lb, the reference light Ls, and the excitation light Le and are sequentially projected onto the target subject 9.

First, the operation occurring when a standard image 11 is to be obtained will be explained. First, when the R light Lr is projected onto the target subject 9, a reflectance image Zr formed of the light reflected from the target subject 9 upon the irradiation thereof by the R light Lr is focused by the focusing lens 215, passed through the excitation cutoff filter 214, reflected by the prism 217, transmitted the wide band filter element 218a of the mosaic filter 218, and detected by the CCD image obtaining element 216.

The reflectance image Zr is received by the CCD image obtaining element 216, and is converted to electric signals corresponding to the intensity level of the photoelectrically converted light.

After the passing of a predetermined period of time, the rotating filter 224 is rotated, and the filter element disposed along the optical path of the white light emitted from the white light source 221 is switched from the R light filtering element 224a to the G light filtering element 224b. At this time, the readout of the signal charge is performed. Note that during the interval in which the signal charge accumulated on the accumulating portion 22 is being read out, the G light Lg is projected onto the target subject 9, and the G light Lg reflected from said target subject 9 is received by the CCD image obtaining element 216 as a reflectance image Zg. Further, the image obtainment operation of the CCD image obtaining element 216 is controlled based on operation control signals inputted thereto from the CCD controller 219.

The output data of the R light reflectance image Zr image is subjected to image processes by the signal processing circuit 131 of the image processing portion 130, digitized by the A/D converting circuit 132, and stored in the R light reflectance image Zr data region of the image memory 133.

Then, the G light reflectance image Zg image data and the B light reflectance image Zb image data are obtained by the same operation as that described above, and stored in the respective G light reflectance image Zg data region and B light reflectance image Zb data region of the image memory 133.

When the three color image data have been stored in the image memory 133, the display timing thereof is synchronized and said three images are outputted simultaneously to the video signal processing circuit 134. The video signal processing circuit 134 converts the inputted signals to video signals and outputs said video signals to the monitor 200; said video signals are displayed thereon as a standard image 11, which is a color image.

Next, the operation occurring when a fluorescence diagnostic image 13 is to be obtained will be explained. The rotating filter 224 is rotated, based on control signals from the controller 150, from the filter element 224c to the filter element 224d; wherein, the filter element 224d is positioned along the optical path of the white light emitted from the white light source 211. In this manner, the reference light Ls, which is a near-infrared light, is projected onto the target subject 9.

The reflectance image Zs formed of the light reflected from the target subject 9 upon the irradiation thereof by the reference light Ls is focused by the focusing lens 215, passed through the excitation cutoff filter 214, reflected by the prism 217, transmitted by the wide band filter element 218a of the rotating filter 218, and detected by the CCD image obtaining element 216.

The reflectance image Zs is received by the CCD image obtaining element 216, converted to electric signals corresponding to the intensity level of the photoelectrically converted light, and outputted to the image signal processing portion 130 in the same manner as described above. The electric signals inputted to the image processing portion 130 are subjected to image processes by the signal processing circuit 131, digitized by the A/D converting circuit 132, and stored as reference image data in the image memory 136.

Next, the operation occurring when a fluorescence image Ze is to be obtained will be explained. The rotating filter 224 is rotated, based on control signals from the controller 150, from the filter element 224d to the filter element 224e; wherein, the filter element 224e is positioned along the optical path of the white light emitted from the white light source 221. In this manner, the excitation light Le is projected onto the target subject 9.

The fluorescence image Ze formed of the light reflected from the target subject 9 upon the irradiation thereof by the excitation light Le is focused by the focusing lens 215, passed through the excitation cutoff filter 214, reflected by the prism 217, transmitted by the wide band filter element 218a and the narrow band filter element 218b of the rotating filter 218, and detected by the CCD image obtaining element 216.

The fluorescence image Ze is received by the CCD image obtaining element 216, photoelectrically converted to an electric signal corresponding to each pixel for the wide band filter element 218a and the narrow band filter element 218b, and outputted to the image signal processing portion 130 in the same manner as described above. The electric signals inputted to the image processing portion 130 are subjected to image processes by the signal processing circuit 131, converted to digital signals by the A/D converting circuit 132, and stored as a wide band fluorescence image data and a narrow band fluorescence image data in the image memory 135.

Next, the operation occurring when the dark noise is to be obtained will be explained. The rotating filter 224 is rotated, based on control signals from the controller 150, from the filter element 224e to the filter element 224f; wherein, the filter element 224f is disposed along the optical path of the white light emitted from the white light source 221. In this manner, light is not projected onto the target subject 9.

At his time, the external light transmitted by the target subject 9 is focused by the focusing lens 215, passed through the excitation cutoff filter 214, reflected by the prism 217, transmitted by the wide band filter element 218a and the narrow band filter element 218b of the rotating filter 218, and detected by the CCD image obtaining element 216.

The external light that has passed through the wide band filter element 218a and the narrow band filter element 218b is received by the CCD image obtaining element 216, converted to electric signals corresponding to the intensity level of the photoelectrically converted light, and outputted to the image signal processing portion 130 in the same manner as described above. The electric signals inputted to the image processing portion 130 are subjected to image processes by the signal processing circuit 131, digitized by the A/D converting circuit 132, and stored as a wide band dark level data and a narrow band dark level data in the dark noise memory 137. Note that these dark noise label data include the data not only of the external light transmitted by the target subject, but also the dark noise of the CCD image obtaining element 216.

When the wide band dark level data and the narrow band dark level data are stored in the dark noise memory 137, the correcting circuit 138 subtracts the wide band dark level data and the narrow band dark level data from the wide band fluorescence image data and the narrow band fluorescence image data stored in the fluorescence image memory 135 to obtain a corrected wide band fluorescence image data and a corrected narrow band fluorescence image data.

When the corrected wide band fluorescence image data and the corrected narrow band fluorescence image data have been obtained, the image forming circuit 139 computes the ratio of the signal intensity between the corresponding pixels of the corrected wide band fluorescence image data and the corrected narrow band fluorescence image data, and applies a color data corresponding to said ratio to obtain a color image data. Further, the signal forming circuit 139 assigns a brightness data to the signal intensity of the reference image data to obtain a brightness image data, and then combines the color image data and the brightness image data to form a composite image data; the composite image data is outputted to the video signal processing circuit 134. The composite image data is converted to video signal by the video signal processing circuit 134 and outputted to the monitor 200. The video signals outputted to the monitor 200 are displayed thereon as a fluorescence diagnostic image 13, which is a false color image.

Figure 7:
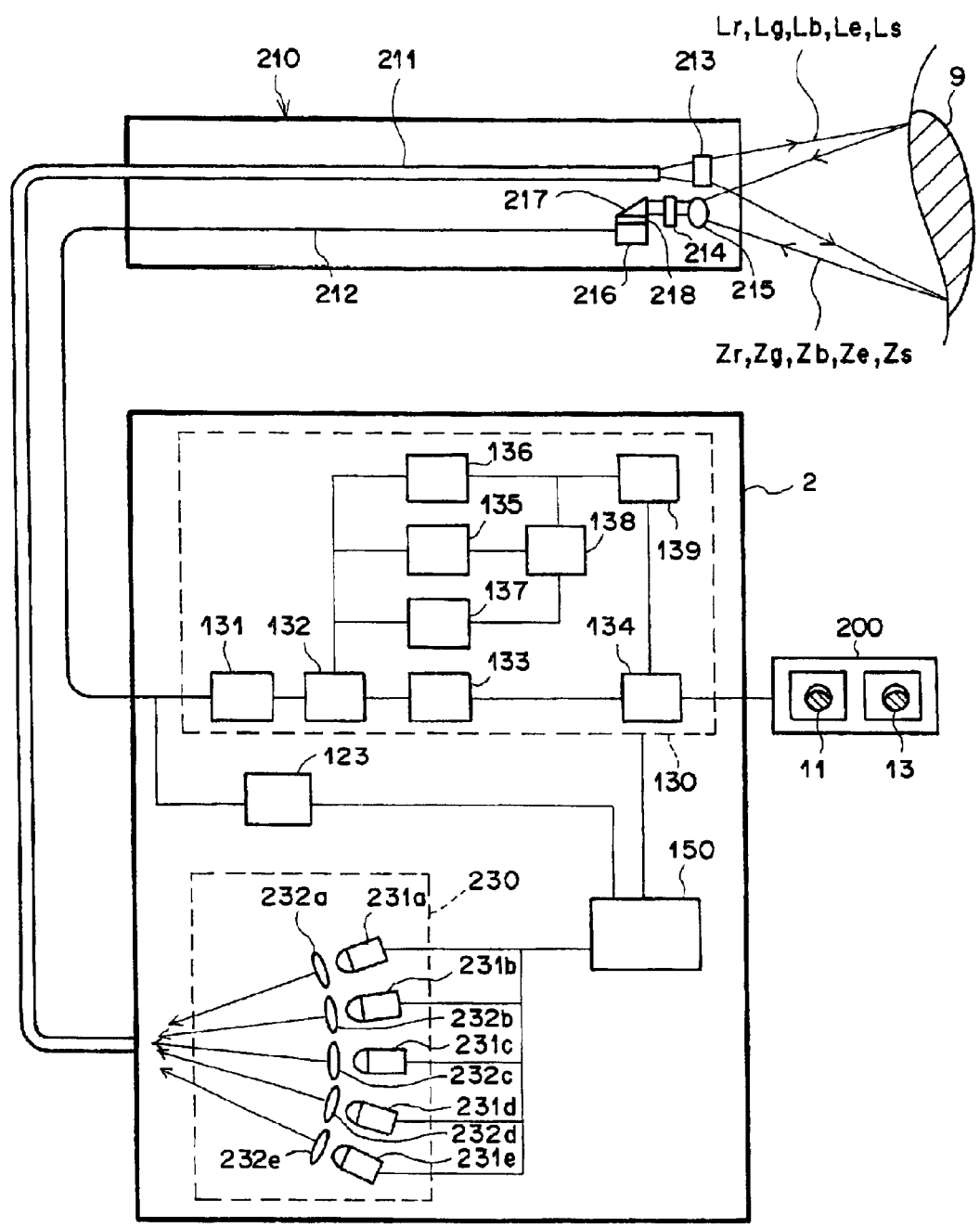
FIG. 7 is a schematic drawing of an endoscope apparatus implementing the image obtaining apparatus according to the third embodiment of the present invention.

Next, the third embodiment will be explained. FIG. 7 is a schematic drawing a fluorescent endoscope apparatus implementing the fluorescence image display apparatus according to third embodiment. Note that elements of the fluorescent endoscope apparatus according to the third embodiment in common with those of the second embodiment are likewise labeled, and further explanation thereof has been omitted. The fluorescent endoscope apparatus according to the third embodiment comprises, instead of the illuminating means 220 of the second embodiment employing the rotating filter 224, an illuminating means 230 provided with light sources 231a–231e, that emit R light Lr, G light Lg, B light Lb, reference light Ls, and excitation light Le, respectively; wherein the emission cycle of each light from said light sources is controlled by the controller 150. Note that each of the light sources 231a–231e is provided with a respective focusing lens 232a–232e for focusing the light emitted therefrom.

The controller 150 activates each light source at a predetermined time interval and in the order of 231a, 231b, 231c, 231d, and 231e; wherein the control of the activation of each said light source 231a–231e is performed so that the cycle of the time interval of emission and the same type of time interval of non-emission is repeated.

In this manner, by controlling the emission cycle of each of the light sources 231a–231e of the illuminating unit 230, the cycle of the emission and shielding of the R light, G light, B light near-infrared light, and the excitation light onto the target subject 9 can be repeated in the same manner as in the second embodiment. Accordingly, by obtaining the reflectance images Zr, Zg, Zb and ZS, and the fluorescence image Ze by the CCD image obtaining element 216 in the same manner as in the second embodiment, a standard image 11 and a fluorescence diagnostic image 13 can be displayed on the monitor 200.

Figure 8:
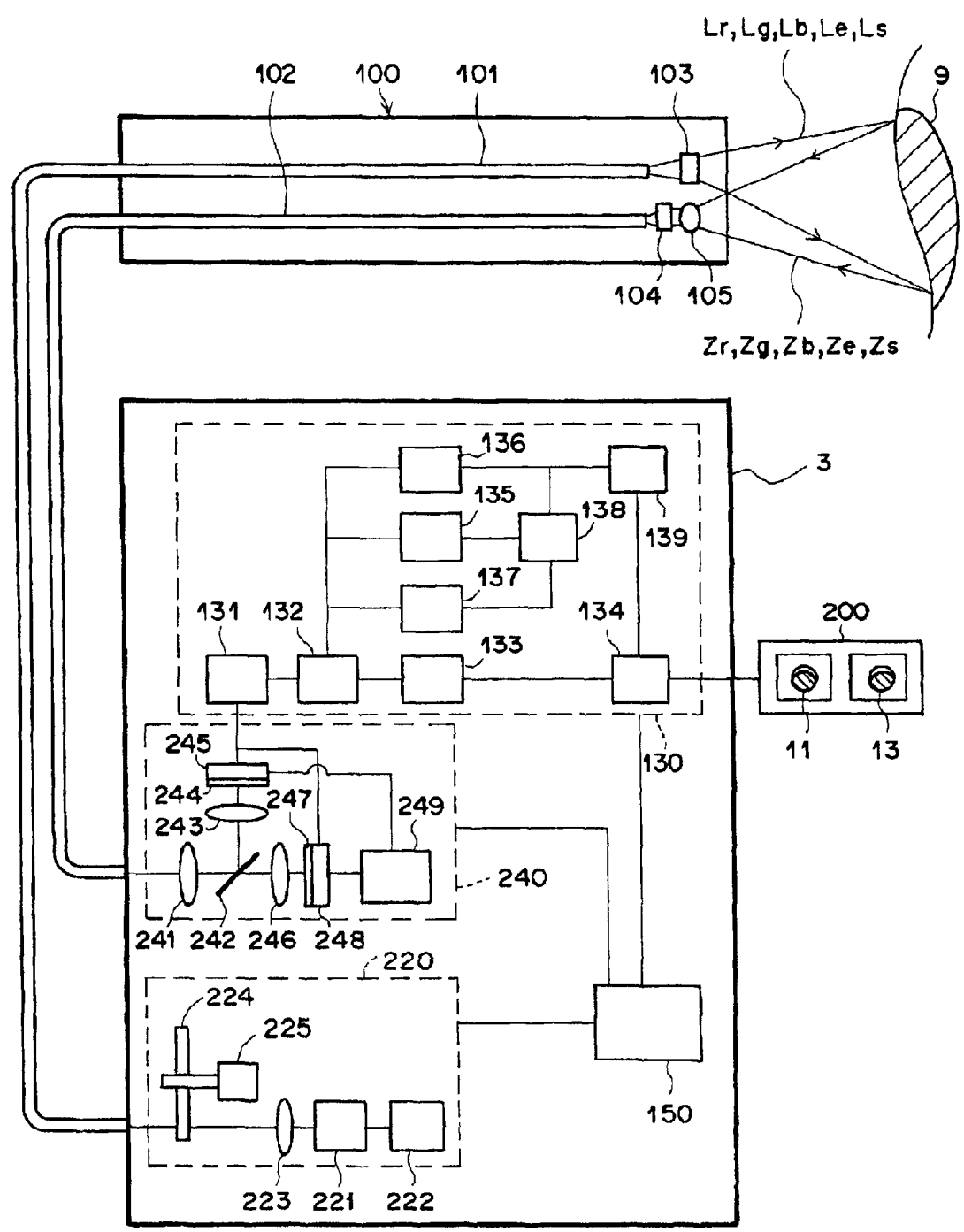
FIG. 8 is a schematic drawing of an endoscope apparatus implementing the image obtaining apparatus according to the fourth embodiment of the present invention.

Next, the fourth embodiment will be explained. FIG. 8 is a schematic drawing of a fluorescent endoscope apparatus implementing the fluorescence image display apparatus according to the fourth embodiment. Note that elements of the fluorescent endoscope apparatus according to the fourth embodiment in common with those of the first and second embodiments are likewise labeled, and further explanation thereof has been omitted. As shown in FIG. 8, the fluorescent endoscope apparatus according to the fourth embodiment comprises: an endoscope insertion portion 100 of the same configuration as that of the first embodiment; an image processing portion 3 for subjecting the image data representing the data obtained of the target subject 9 to image processes; and a monitor 200 of the same configuration as that of the first embodiment for displaying as a color image the image data processed by the image processing portion 3.

The image processing portion 2 comprises: an illuminating unit 220 for emitting illuminating light; a CCD controller 219 for controlling the operations of the CCD image obtaining element 216; an image detecting unit 240 for digitizing the obtained images and outputting image data thereof; an image processing unit 130, which is the same as that of the first embodiment; and a controller 150, which is the same as that of the first embodiment, for controlling the operation of each unit.

The image detecting unit 240 comprises: a collimator lens 241 that is connected to the image fiber 102 and which focuses an optical image conveyed thereto via the image fiber 102; a half mirror 242 that transmits 50% and reflects 50%, in a direction not shown in the drawing, of the light of the optical image transmitted by the collimator lens 241; a focusing lens 243 for focusing the optical image reflected by the half mirror 242; a narrow band filter 244 for extracting light having a wavelength in the 430–530 nm wavelength range from the optical image transmitted by the focusing lens 243; a charge multiplying type CCD image obtaining element 245 for obtaining the optical image transmitted by the narrow band filter 244; a focusing lens 246 for focusing the optical image transmitted by the half mirror 242; a wide band filter 247 for extracting light having a wavelength in the 400–900 nm wavelength range from the optical image transmitted by the focusing lens 246; a charge multiplying type CCD image obtaining element 248 for obtaining the optical image transmitted by the wide band filter 247; and a CCD controller 249 for controlling the operation of the CCD image obtaining elements 245 and 248. Note that the CCD image obtaining elements 245 and 248 are of the same configuration of the CCD image obtaining element 122 of the first embodiment.

Hereinafter the operation of the endoscope according to the fourth embodiment will be explained. The endoscope apparatus according to the fourth embodiment, in the same manner as the endoscope apparatus of the first embodiment, performs the obtainment of the reflectance images Zr, Zg and Zb, the reflectance image Zs, the fluorescence image Ze, and the detection of the dark matter in a time division manner; wherein a standard image 11 base on the reflectance images Zr, Zg and Zb, and a fluorescence diagnostic image based on the reflectance image Zs and the fluorescence image Ze are displayed on a monitor 200. Because each optical image is obtained in a time division manner, the rotating filter 224 of the illuminating unit 220 is rotated, and by passing the white light emitted from the white light source 221 through the rotating filter 224, the R light Lr, G light Lg, B light Lb, the reference light Ls, and the excitation light Le and are sequentially projected onto the target subject 9.

First, the operation occurring when a standard image 11 is to be obtained will be explained. First, when the R light Lr is projected onto the target subject 9, a reflectance image Zr formed of the light reflected from the target subject 9 upon the irradiation thereof by the R light Lr is focused by the focusing lens 105, passed through the excitation light cutoff filter 104 and enters the distal end of the image fiber 102; then, said reflectance image Zr enters the image detecting unit 240.

The reflectance image Zr entering the image detecting unit 240 is transmitted by the collimator lens 241, the half mirror 242, the focusing lens 246 and the wide band filter 247, and is focused on the CCD image obtaining element 248. Note that at this time, the reflectance image Zr reflected by the half mirror 242 is also focused on the CCD image obtaining element 245; however, the signal from the CCD image obtaining element 245 is not read out while the reflectance images Zr, Zg, Zb, and Zs are being obtained.

The reflected image Zr is received by the CCD image obtaining element 248, and converted to electric signals corresponding to the intensity level of the photoelectrically converted light.

After the passing of a predetermined period of time, the rotating filter 224 is rotated, and the filter element disposed along the optical path of the white light emitted from the white light source 221 is switched from the R light filtering element 224a to the G light filtering element 224b. At this time, the readout of the signal charge is performed. Note that during the interval in which the signal charge accumulated on the accumulating portion 22 is being read out, the G light Lg is projected onto the target subject 9, and the G light Lg reflected from said target subject 9 is received by the CCD image obtaining element 248 as a reflectance image Zg. Further, the image obtainment operation of the CCD image obtaining element 248 is controlled based on operation control signals inputted thereto from the CCD controller 249.

The output data of the R light reflectance image Zr image is subjected to image processes by the signal processing circuit 131 of the image processing portion 130, digitized by the A/D converting circuit 132, and stored in the R light reflectance image Zr data region of the image memory 133.

Then, the G light reflectance image Zg image data and the B light reflectance image Zb image data are obtained by the same operation as that described above, and stored in the respective G light reflectance image Zg data region and B light reflectance image Zb data region of the image memory 133.

When the three color image data have been stored in the image memory 133, the display timing thereof is synchronized and said three images are outputted simultaneously to the video signal processing circuit 134. The video signal processing circuit 134 converts the inputted signals to video signals and outputs said video signals to the monitor 200; said video signals are displayed thereon as a standard image 11, which is a color image.

Next, the operation occurring when a fluorescence diagnostic image 13 is to be obtained will be explained. The rotating filter 224 is rotated, based on control signals from the controller 150, from the filter element 224c to the filter element 224d; wherein, the filter element 224d is positioned along the optical path of the white light emitted from the white light source 211. In this manner, the reference light Ls, which is a near-infrared light, is projected onto the target subject 9.

The reflectance image Zs formed of the light reflected from the target subject 9 upon the irradiation thereof by the reference light Ls is focused by the focusing lens 105, passed through the excitation light cutoff filter 104, and enters the distal end of the image fiber 102; then, the reflectance image Zs enters the image detecting unit 240 in the same manner as the reflectance images Zr, Zg, and Zb, and is focused on the CCD image obtaining element 248.

The reflectance image Zs is received by the CCD image obtaining element 248, converted to electric signals corresponding to the intensity level of the photoelectrically converted light, and outputted to the image signal processing portion 130 in the same manner as described above. The electric signals inputted to the image processing portion 130 are subjected to image processes by the signal processing circuit 131, digitized by the A/D converting circuit 132, and stored as reference image data in the image memory 136.

Next, the operation occurring when a fluorescence image Ze is to be obtained will be explained. The rotating filter 224 is rotated, based on control signals from the controller 150, from the filter element 224d to the filter element 224e; wherein, the filter element 224e is positioned along the optical path of the white light emitted from the white light source 221. In this manner, the excitation light Le is projected onto the target subject 9.

The fluorescence image Ze formed of the light reflected from the target subject 9 upon the irradiation thereof by the excitation light Le is focused by the focusing lens 105, passed through the excitation light cutoff filter 104, and enters the distal end of the image fiber 102; then, the fluorescence image Ze enters the image detecting unit 240.

The fluorescence image Ze entering the image detecting unit 240 is transmitted by the collimator lens 241, the half mirror 242, the focusing lens 246 and the wide band filter 247, and is focused on the CCD image obtaining element 248. On the other hand, the fluorescence image Ze reflected by the half mirror 242 is transmitted by the focusing lens 243 and the narrow band filter 244, and focused on the CCD image obtaining element 245.

The wide band fluorescence image Ze is received by the CCD image obtaining element 248, and converted to electric signals corresponding to the intensity level of the photoelectrically converted light. The narrow band fluorescence image Ze is received by the CCD image obtaining element 245, and converted to electric signals corresponding to the intensity level of the photoelectrically converted light.

The output data of the wide band fluorescence image Ze and the narrow band fluorescence image Ze outputted from the the CCD image obtaining elements 245 and 248 is inputted to the image signal processing portion 130. The electric signals inputted to the image processing portion 130 are subjected to image processes by the signal processing circuit 131, converted to digital signals by the A/D converting circuit 132, and stored as a wide band fluorescence image data and a narrow band fluorescence image data in the image memory 135.

Next, the operation occurring when the dark noise is to be obtained will be explained. The rotating filter 224 is rotated, based on control signals from the controller 150, from the filter element 224e to the filter element 224f; wherein, the filter element 224f is disposed along the optical path of the white light emitted from the white light source 221. In this manner, light is not projected onto the target subject 9.

At his time, the external light transmitted by the target subject 9 is focused by the focusing lens 105, passed through the excitation light cutoff filter 104, and enters the distal end of the image fiber 102; then, the fluorescence image Ze enters the image detecting unit 240. The external light entering the image detecting unit 240 is transmitted by the collimator lens 241, and a portion thereof is transmitted by the half mirror 242, the focusing lens 246 and the wide band filter 247, and is focused on the CCD image obtaining element 248. On the other hand, the external light reflected by the half mirror 242 is transmitted by the focusing lens 243 and the narrow band filter 244, and focused on the CCD image obtaining element 245.

The wide band external light is received by the CCD image obtaining element 248, and converted to electric signals corresponding to the intensity level of the photoelectrically converted light. The narrow band external light is received by the CCD image obtaining element 245, and converted to electric signals corresponding to the intensity level of the photoelectrically converted light.

The output data of the wide band external light and the narrow band external light outputted from the CCD image obtaining elements 245 and 248 is inputted to the image signal processing portion 130. The electric signals inputted to the image processing portion 130 are subjected to image processes by the signal processing circuit 131, converted to digital signals by the A/D converting circuit 132, and stored as a wide band dark level data and a narrow band dark level data in the image memory 137. Note that these dark level data include not only the data of the external light transmitted by the target subject, but also that of the dark noise of the CCD image obtaining elements 245 and 248.

When the wide band dark level data and the narrow band dark level data are stored in the dark noise memory 137, the correcting circuit 138 subtracts the wide band dark level data and the narrow band dark level data from the wide band fluorescence image data and the narrow band fluorescence image data stored in the fluorescence image memory 135 to obtain a corrected wide band fluorescence image data and a corrected narrow band fluorescence image data.

When the corrected wide band fluorescence image data and the corrected narrow band fluorescence image data have been obtained, the image forming circuit 139 computes the ratio of the signal intensity between the corresponding pixels of the corrected wide band fluorescence image data and the corrected narrow band fluorescence image data, and applies a color data corresponding to said ratio to obtain a color image data. Further, the signal forming circuit 139 assigns a brightness data to the signal intensity of the reference image data to obtain a brightness image data, and then combines the color image data and the brightness image data to form a composite image data; the composite image data is outputted to the video signal processing circuit 134. The composite image data is converted to video signal by the video signal processing circuit 134 and outputted to the monitor 200. The video signals outputted to the monitor 200 are displayed thereon as a fluorescence diagnostic image 13, which is a false color image.

Note that according to the fourth embodiment, the illuminating unit 220, which is the same as that of the second embodiment, has been employed; however, it is also possible to employ the same illuminating unit 230 as that of the third embodiment.

Further, according to the fourth embodiment, the optical image guided by the image fiber 102 has been subjected to image processes by the image detecting unit 240 of the image processing portion 3; however, an image detecting unit corresponding to the image detecting unit 240 can be provided downline of the means after the excitation cutoff filter, and after the received optical image has been converted to electric signals can be transmitted from the endoscope insertion portion 100 to the image processing unit 130 of the image data processing portion 3. In this manner, because the optical image can be detected without having been conveyed by the image fiber 102, the resolution of the obtained image can be improved, and the loss in the light quantity of the image incurred during the conveyance thereof through the image fiber 102 can be prevented.

What is claimed is:

1. An image obtaining apparatus comprising:
    a light emitting means for projecting an illuminating light that includes an excitation light onto a target subject,
    a charge multiplying type solid state image obtaining element for obtaining an optical image based on the re-radiated light, which contains fluorescent light, generated by the target subject upon the irradiation thereof by the illuminating light, and obtaining an output data representing the obtained optical image,
    a filter means for extracting at least two different wavelength ranges from said fluorescent light so that said solid state image obtaining element can obtain fluorescence images based on fluorescent light of said different wavelength ranges, and
    a correcting means for detecting dark noise generated by the solid state image obtaining element, and correcting the output data, based on the detected dark noise, to obtain a corrected output data, wherein
    said correcting means is a means for correcting the output data representing the fluorescence images.

2. An image obtaining apparatus as defined in claim 1, wherein said correcting means is a means for performing the steps of:
    causing the emission of the illuminating light from the light emitting means onto the target subject to be paused periodically at regular intervals,
    detecting the dark noise based on the output signal obtained by the solid state image obtaining element during the interval in which the emission of said illuminating light has been paused, and
    correcting, based on the detected dark noise, the output data obtained by the solid state image obtaining element during the interval in which the illuminating light has been projected onto the target subject to obtain a corrected output data.

3. An image obtaining apparatus as defined in claim 2, wherein
    said filter means is a rotating filter means having at least two filter elements, each of which transmits a different wavelength range of light, wherein
        by the rotation of the different filter elements, each of said filter elements can be made to positionally correspond with a light receiving surface of the solid state image obtaining element.

4. An image obtaining apparatus as defined in claim 2, wherein
    said filter means is provided on a light receiving surface of the solid state image obtaining element, and formed of a combination of two or more types of filter elements, each of which transmits a different wavelength range of light, disposed alternately on a two-dimensional flat surface.

5. An image obtaining apparatus as defined in any of the claims 1 or 2, wherein
    a portion or the entirety of the light emitting means and the solid state image obtaining element can be provided in the form of an endoscope for insertion into a body cavity of a patient.

6. An image obtaining apparatus as defined in either of claims 3 or 4, wherein
    a portion or the entirety of the light emitting means and the solid state image obtaining element can be provided in the form of an endoscope for insertion into a body cavity of a patient.

7. An image obtaining apparatus as defined in claim 1, wherein
    said filter means is a rotating filter means having at least two filter elements, each of which transmits a different wavelength range of light, wherein
        by the rotation of the different filter elements, each of said filter elements can be made to positionally correspond with a light receiving surface of the solid state image obtaining element.

8. An image obtaining apparatus as defined in claim 7, wherein
    a portion or the entirety of the light emitting means and the solid state image obtaining element can be provided in the form of an endoscope for insertion into a body cavity of a patient.

9. An image obtaining apparatus as defined in claim 1, wherein
    said filter means is provided on a light receiving surface of the solid state image obtaining element, and formed of a combination of two or more types of filter elements, each of which transmits a different wavelength range of light, disposed alternately on a two-dimensional flat surface.

10. An image obtaining apparatus as defined in claim 9, wherein a portion or the entirety of the light emitting means and the solid state image obtaining element can be provided in the form of an endoscope for insertion into a body cavity of a patient.

11. The apparatus of claim 1, wherein said filter means comprises a narrow band filter element and a wide band filter element providing outputs to the image obtaining element.

12. The apparatus of claim 11, wherein said light emitting means alternately emits the illuminating light of red, green, and blue wavelengths, an infrared wavelength, and an excitation wavelength, wherein the wide band filter element is disposed to provide outputs of red, green, blues, infrared and wide band fluorescence images to the image obtaining element and the narrow band filter element is disposed to provide output of a narrow band fluorescence image to the image obtaining element.

13. The apparatus of claim 12, wherein said light emitting means comprises a light source and light source filter means for alternately extracting from light emitted by the light source said illuminating light of red, green, and blue wavelengths, and infrared wavelength, and wherein said filter means and said light source filter means are formed as an integrated rotational filter.

14. The apparatus of claim 1 further comprising a blocking device to block the illuminating light, wherein dark noise is determined by reading an image when the blocking device is disposed to block the illuminating light.

15. The apparatus of claim 14, wherein a ratio of a wide band dark image to a narrow band dark image is used to correct for dark noise.

* * * * *